(12) United States Patent
Irvin et al.

(10) Patent No.: US 7,446,208 B1
(45) Date of Patent: Nov. 4, 2008

(54) PROCESS FOR MAKING TETRAZOLE BASED LINEAR POLYMERS

(75) Inventors: David J. Irvin, Ridgecrest, CA (US); Mark H. Mason, Inyokern, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 445 days.

(21) Appl. No.: 11/151,179

(22) Filed: May 27, 2005

(51) Int. Cl.
*C07D 257/04* (2006.01)
(52) U.S. Cl. ...................................................... 548/250
(58) Field of Classification Search .................. 514/381; 548/250
See application file for complete search history.

(56) References Cited

OTHER PUBLICATIONS

Copending U.S. Appl. No. 11/151,178, filed May 27, 2005.*
National Institute of Standards and Technology 1H-Tetrazole data sheet, Feb. 26, 2008, 1 pg, http://webbook.nist.gov/chemistry.

* cited by examiner

*Primary Examiner*—Rei-tsang Shiao
*Assistant Examiner*—Susannah Chung
(74) *Attorney, Agent, or Firm*—Brian F. Drazich; Charlene A. Haley

(57) ABSTRACT

A process for preparation of polymers including reacting an effective amount of tetrazole diols or tetrazole polyols with isocyanate resins to produce tetrazole based linear isocyanate polymers.

18 Claims, No Drawings

PROCESS FOR MAKING TETRAZOLE BASED LINEAR POLYMERS

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND OF THE INVENTION

There is a need for novel energetic binders to increase the performance of pyrotechnics, gun propellants, rocket propellants, air-bag gas generator propellants, and explosives. Depending on the application, these materials are typically 3-25% binder by mass. Therefore, improvements to the energy content, mechanical properties, or insensitive munitions properties of the polymeric binder can have significant affects on the performance of the energetic material in question.

In general many pyrotechnics, propellants, explosives are comprised of a polymeric binder that holds one or more energetic solids in a plastic matrix. The polymeric binder serves many roles in these materials. Initially the polymer can aid in processing. In fact, the properties of the polymer will significantly affect how a material is processed, whether it is cast or pressed or extruded. Furthermore, the polymer mechanically holds all the ingredients together, serving as a structural element literally binding together the final material. This role is especially critical in rocket propellants, because cracks and voids in the propellant will lead to motor grain failure, often with catastrophic results. The binder serves many safety functions. The binder physically coats the energetic solids in these materials, thus provides a physical buffer to minimize the physical and chemical interaction of reactive solids with each other. This generally lowers the electrostatic discharge, impact, and friction sensitivity of the final material. In some materials, especially rocket propellants, the binder also serves as a fuel when the hydrocarbon polymer is combusted by the oxidizer. However, the binder generally diminishes the performance (detonation pressure and velocity) of most explosives. To improve the performance of explosives with significant binder content, and to increase the energy density of propellants energetic polymers are needed.

While there are energetic binders available (polyglycidyl nitrate (PGN), polyglycidyl azide (GAP), azidomethyl-methyl-oxetane (AMMO), bis((azido-methyl)oxetane) (BAMMO), nitratomethyl-methyloxetane (NMMO), etc.) the safety benefits of increasing binder content are lost because these materials contain either organic azides or nitrate esters (or both). These functional groups are chemically unstable, easily ignited, and generally create reactive fragments on aging. In fact, propellants that utilize nitrate esters generally require expensive monitoring programs throughout their life cycle to insure both adequate safety properties and performance as the propellant ages. The cost of such monitoring is often cited as one reason most modern explosives do not to use nitrate esters as binder materials. Furthermore, the energetic groups are pendant moieties attached to the polymer, but not incorporated into the polymer backbone. This impairs the physical properties of these polymers and causes the formulator to need a higher weight percent of binder in order to achieve adequate coating. In short, there is a need for improved energetic binders to address safety, performance, aging, and processing requirements.

While tetrazoles are somewhat less energetic than azides or nitrates, the bis-alkyltetrazoles of interest are more thermally stable and substantially less chemically reactive. Higher percentages of these binders could be used without anticipating negative safety consequences. Furthermore, the energetic functionality is built into the polymer backbone, minimizing the total moles of pendant atoms. This is anticipated to yield a binder with superior physical properties. A dihydroxy-terminated bis-tetrazole (2,2 Bis((2-ethanol)-1 or 2H-tetrazole)-propane or BETP) has been synthesized on the multigram scale. Initial differential scanning calorimetry (DSC) analysis shows this pre-polymer has promise as an energetic cured urethane binder for explosives and propellants and gas generators.

U.S. Pat. No. 5,053,086 issued on Oct. 1, 1991 to Henry, et al., which teaches gas generating compositions containing energetic high nitrogen such as ammonium 5-nitraminotetrazole and 5,5'-bitetrazole. This work yielded polymeric binders that are too rigid and "glassy" for the intended application. The chemical structure of the present invention polymers builds more flexibility into the backbone, yielding improved elastomers. Further research by Demko teaches the addition of sodium azide to nitriles to give 1H-tetrazoles in water with zinc salts as catalysts. (Demko, Z. P.; Sharpless, K. B. "Preparation of 5-substituted 1H-tetrazoles from nitriles in water." *J. Org. Chem.* 2001, 66, 7945). This step is only one method to obtain the tetrazole intermediate. Further reaction is necessary to produce the alcohol-based monomers. The addition of the alkyl alcohol is two fold: first, the short alkyl chain adds flexibility, solubility; second, the alcohol group allows for the production of stable polyurethanes. Polymerization of the tetrazole would produce the less stable polyurea.

Tetrazole compounds have application in many fields including, but not limited to, chemistry, ligands, metabolically stable surrogate for a carboxylic acid group, and material sciences including explosives and propellants and air bag gas generators.

It is to be understood that the foregoing general description and the following detailed description are exemplary and explanatory only and are not to be viewed as being restrictive of the present invention, as claimed. Further advantages of this invention will be apparent after a review of the following detailed description of the disclosed embodiments and in the appended claims.

DETAILED DESCRIPTION OF THE INVENTION

Embodiments of the present invention generally relate to a process for making energetic cast cured binders by using tetrazole diols and isocyanate resins for making tetrazole based linear polyisocyanate polymers. Other embodiments of the present invention relate to a process for preparation of a polymer having the general structure (I) comprising: reacting an effective amount

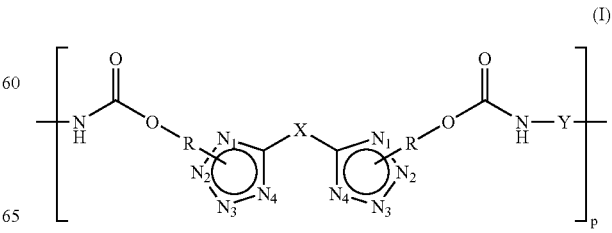

of tetrazole diol having the general structure (II) with isocyanate resin, wherein [X] comprises at least one group of alkyls, aryls, and oligoethers, wherein [R] comprises at least one group of alkyls, aryls, and oligoethers, wherein [R] is chemically bonded to $N_1$ or $N_2$ position; wherein the

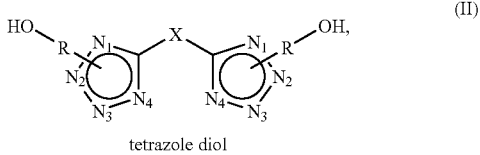

tetrazole diol isocyanate resin having the general structure (III), wherein [Y] comprises at least one group of alkyls, aryls, and oligoethers, at a temperature in the range of about 50° C. to about 100° C. for a time period in the range of about 1 to about 48 hours; and cooling to room temperature producing a

linear polyisocyanate polymer having the general structure (I), wherein [X] comprises at least one group of alkyls, aryls, and oligoethers, wherein [Y] comprises at least one group of alkyls, aryls, and oligoethers, wherein [p] is about 5 about 10,000, wherein [R] comprises at least one group of alkyls, aryls, and oligoethers, wherein [R] is chemically bonded to $N_1$ or $N_2$ position of the linear polyisocyanate polymer (I).

Other embodiments of the present invention relate to a process for preparation of a polymer having the general structure (IV) comprising: reacting an effective amount of tetrazole polyol

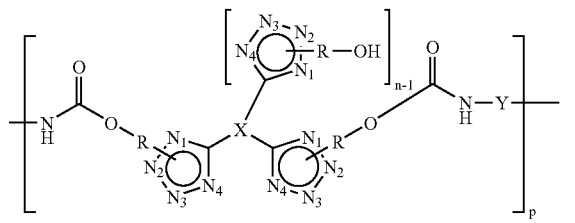

having the general structure (V) with isocyanate resin, wherein [X] of the tetrazole polyol comprises at least one group of alkyls, aryls, and oligoethers, wherein [n] is 2 to 9, wherein [R] comprises at least one group of alkyls, aryls, and oligoethers, wherein [R] is chemically bonded to $N_1$ or $N_2$ position; wherein the isocyanate resin having the general structure (III), wherein [Y]

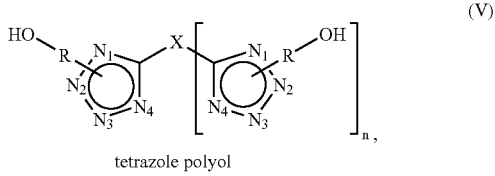

tetrazole polyol comprises at least one group of alkyls, aryls, and oligoethers, at a temperature in the range of about 50° C. to about 100° C. for a time period in the range of about 1 to about 48 hours; and cooling to room temperature producing a linear polyisocyanate polymer having the general structure (IV),

wherein [X] comprises at least one group of alkyls, aryls, and oligoethers, wherein [n] is 2 to 9, wherein [p] is about 5 to about 10,000, wherein [Y] comprises at least one group of alkyls, aryls, and oligoethers, wherein [R] comprises at least one group of alkyls, aryls, and oligoethers, wherein [R] is chemically bonded to $N_1$ or $N_2$ of the linear polyisocyanate polymer (IV).

When the tetrazole polyol is alkylated tetrazole polyol, the alkylated tetrazole polyol includes tri-alkylated tetrazole polyol. When the tetrazole polyol is alkylated tetrazole polyol, the alkylated tetrazole polyol includes tetra-alkylated tetrazole polyol.

Yet other embodiments of the present invention include a process for preparation of a polymer having the general structure (VI) comprising: reacting an effective amount of tetrazole

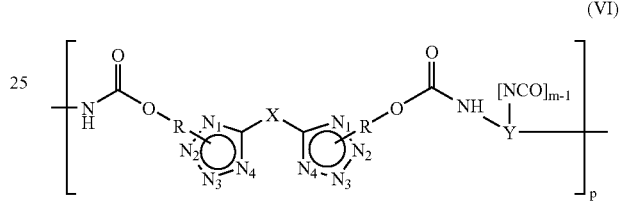

diol having the general structure (II) with isocyanate resin, wherein [X] of the tetrazole diol comprises at least one group of alkyls, aryls, and oligoethers, wherein [R] comprises at least one group of alkyls, aryls, and oligoethers, wherein [R] is chemically bonded to $N_1$ or $N_2$ position;

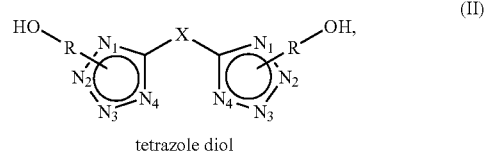

tetrazole diol wherein the isocyanate resin having the general structure (VII), wherein [Y] comprises at least one group of alkyls, aryls, and oligoethers, wherein [m] is 2-9, at a temperature in the range of about 50° C. to about 100° C. for a time period in the range of about 1 to about 48 hours; and cooling to

room temperature producing a linear polyisocyanate polymer having the general structure (VI), wherein [X] comprises at least one group of alkyls, aryls, and oligoethers, wherein [Y] comprises at least one group of alkyls, aryls, and oligoethers, wherein [m] is 2 to 9, wherein [p] is about 5 to about 10,000, wherein [R] comprises at least one group of alkyls, aryls, and oligoethers, wherein [R] is chemically bonded to $N_1$ or $N_2$ position of the linear polyisocyanate polymer (VI).

When tetrazole diol is alkylated tetrazole diol, the alkylated tetrazole diol includes di-alkylated tetrazole. When tetrazole diol is arylated tetrazole diol, the arylated tetrazole diol includes di-arylated tetrazole. In other embodiments, [p] of the linear polyisocyanate polymer is about 5 to about 1,000. Embodiments of the present invention further include combining at least one catalyst and filler together with the tetrazole diol (II) and the isocyanate resin.

Although all embodiments of the present invention include any combinations of [R], [X] and [Y], the following are examples of some genus and species embodiments. The [R], [X] and [Y] of the linear polyisocyanate polymers (I), (IV), and (VI), include any combination thereof:

| R | X | Y |
|---|---|---|
|  | —(CH$_2$)— |  |
|  | —(CH$_2$)— |  |
|  | —(CH$_2$)— |  |
|  | —(CH$_2$)— | 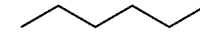 |
|  | —(CH$_2$)— |  |
|  | —(CH$_2$)— |  |
|  | —(CH$_2$)— | 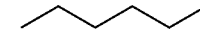 |
|  | —(CH$_2$)— |  |
|  | —(CH$_2$)— |  |
|  | 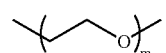 | 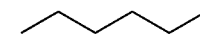 |
|  | 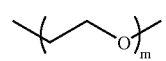 |  |
|  |  | 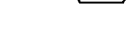 |
|  | 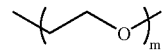 |  |
|  | 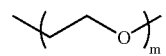 |  |

-continued

| R | X | Y |
|---|---|---|
|  | 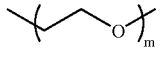 | 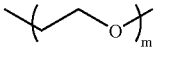 |
| 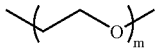 | 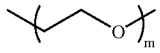 | 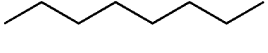 |
| 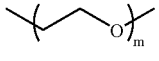 | 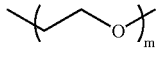 | 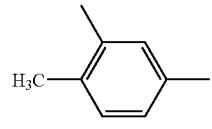 |
| 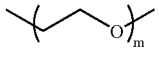 | 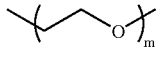 | 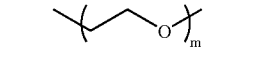 |
| 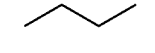 | 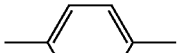 | 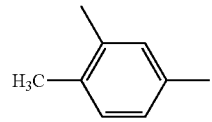 |
| 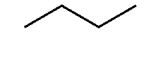 | 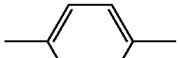 | 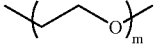 |
|  | 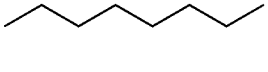 | 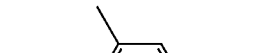 |
|  | 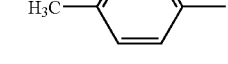 |  |
| 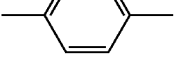 |  | 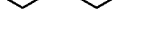 |
| 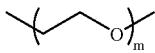 | 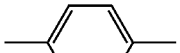 | 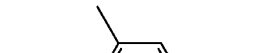 |
|  |  | 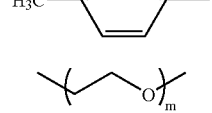 |
|  | 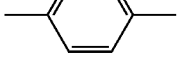 |  |

Experimental Result

Example of Polymerization

Difunctional Tetrazole with Difunctional Isocyanate

In a glass vial equipped with a stir bar, dihydroxy(2,2-dimethyl) bis tetrazole (95 mg), hexamethylene di-isocyanate (60 mg), tetrahydrofuran (5 mL) and dimethylaminopyridine catalyst were combined and stirred at 65° C. for 2 hours, to yield a pale yellow solid rubber. The solid was analyzed by DSC.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A process for preparation of a polymer of structure (I) comprising:

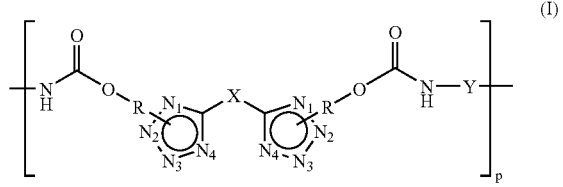
(I)

wherein "X" is a group consisting of at least one of alkyl, aryl, and oligoether, wherein "Y" is a group consisting of at least one of alkyl, aryl, and oligoether, wherein "p" is about 5 to about 10,000, wherein "R" is at least one group of alkyls, aryls, and oligoethers, and wherein "R" is chemically bonded to $N_1$ or $N_2$ position;

reacting an isocyanate resin with an effective amount of a tetrazole diol of structure (II),

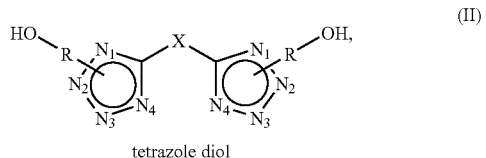
(II)

tetrazole diol at a temperature in the range from about 50° C. to about 100° C. for a time period in the range from about 1 hour to about 48 hours, wherein "X" is a group consisting of at least one of alkyl, aryl, and oligoether, wherein "R" is a group consisting of at least one of alkyl, aryl, and oligoether, wherein "R" is chemically bonded to $N_1$ or $N_2$ position;

said isocyanate resin of structure (III),

OCN—Y—NCO (III), wherein "Y" is a group consisting of at least one of alkyl, aryl, and oligoether;

cooling to room temperature;

extracting a linear polyisocyanate polymer of structure (I).

2. The process according to claim 1, wherein said tetrazole diol is alkylated tetrazole diol, said alkylated tetrazole diol is di-alkylated tetrazole.

3. The process according to claim 1, wherein said tetrazole diol is arylated tetrazole diol, said arylated tetrazole diol is di-arylated tetrazole.

4. The process according to claim 1, wherein said "p" of said linear polyisocyanate polymer is about 5 to about 1,000.

5. The process according to claim 1, further comprising combining together with said tetrazole diol (II) and said isocyanate resin, a catalyst selected from the group of catalysts consisting of zinc salts and dimethylaminopyridine.

6. The process according to claim 1, wherein said polymer having the structure (I), "R", "X" and "Y" include any combination thereof:

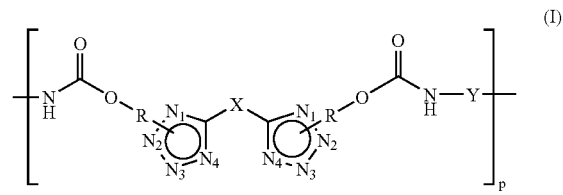
(I)

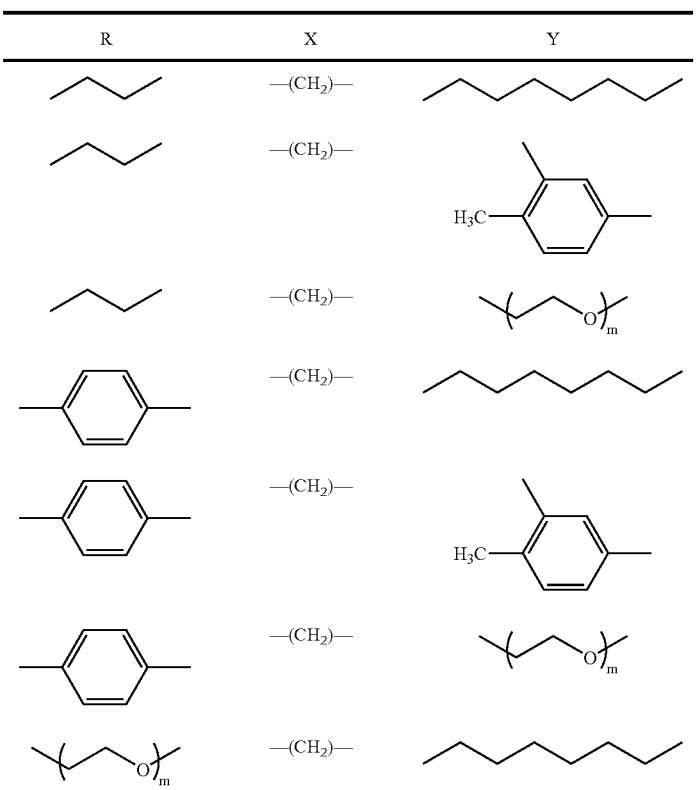

-continued

| R | X | Y |
|---|---|---|
| $-(\text{CH}_2\text{CH}_2\text{O})_m-$ | $-(\text{CH}_2)-$ | 2,4-dimethylphenyl (with $H_3C$) |
| $-(\text{CH}_2\text{CH}_2\text{O})_m-$ | $-(\text{CH}_2)-$ | $-(\text{CH}_2\text{CH}_2\text{O})_m-$ |
| propyl | $-(\text{CH}_2\text{CH}_2\text{O})_m-$ | heptyl |
| propyl | $-(\text{CH}_2\text{CH}_2\text{O})_m-$ | 2,4-dimethylphenyl |
| propyl | $-(\text{CH}_2\text{CH}_2\text{O})_m-$ | $-(\text{CH}_2\text{CH}_2\text{O})_m-$ |
| 1,4-phenylene | $-(\text{CH}_2\text{CH}_2\text{O})_m-$ | heptyl |
| 1,4-phenylene | $-(\text{CH}_2\text{CH}_2\text{O})_m-$ | 2,4-dimethylphenyl |
| 1,4-phenylene | $-(\text{CH}_2\text{CH}_2\text{O})_m-$ | $-(\text{CH}_2\text{CH}_2\text{O})_m-$ |
| $-(\text{CH}_2\text{CH}_2\text{O})_m-$ | $-(\text{CH}_2\text{CH}_2\text{O})_m-$ | heptyl |
| $-(\text{CH}_2\text{CH}_2\text{O})_m-$ | $-(\text{CH}_2\text{CH}_2\text{O})_m-$ | 2,4-dimethylphenyl |
| $-(\text{CH}_2\text{CH}_2\text{O})_m-$ | $-(\text{CH}_2\text{CH}_2\text{O})_m-$ | $-(\text{CH}_2\text{CH}_2\text{O})_m-$ |
| propyl | 1,4-phenylene | heptyl |
| propyl | 1,4-phenylene | 2,4-dimethylphenyl |
| propyl | 1,4-phenylene | $-(\text{CH}_2\text{CH}_2\text{O})_m-$ |
| 1,4-phenylene | 1,4-phenylene | heptyl |

-continued

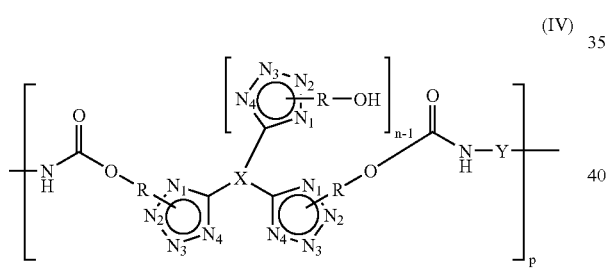

7. A process for preparation of a polymer of structure (IV) comprising:

(IV)

wherein "X" is a group consisting of at least one of alkyl, aryl, and oligoether, wherein "n" is 2 to 9, wherein "p" is about 5 to about 10,000, wherein "Y" is a group consisting of at least one of alkyl, aryl, and oligoether, wherein "R" is a group consisting of at least one of alkyl, aryl, and oligoether, wherein "R" is chemically bonded to $N_1$ or $N_2$ position;

reacting an isocyanate resin with an effective amount of a tetrazole polyol of structure (V), (V)

tetrazole polyol at a temperature in the range from about 50° C. to about 100° C. for a time period in the range from about 1 hour to about 48 hours, wherein "X" is a group consisting of at least one of alkyl, aryl, and oligoether, wherein "R" is a group consisting of at least one of alkyl, aryl, and oligoether, wherein "R" is chemically bonded to $N_1$ or $N_2$ position;

said isocyanate resin of structure (III),

OCN—Y—NCO      (III), wherein "Y" is at least one of alkyl, aryl, and oligoether;
cooling to room temperature;
extracting a linear polyisocyanate polymer of structure (IV).

8. The process according to claim 7, wherein said tetrazole polyol is alkylated tetrazole polyol, said alkylated tetrazole polyol is tri-alkylated tetrazole polyol.

9. The process according to claim 7, wherein said tetrazole polyol is alkylated tetrazole polyol, said alkylated tetrazole polyol is tetra-alkylated tetrazole polyol.

10. The process according to claim 7, wherein said polymer having the structure (IV), "R", "X", and "Y" include any combination thereof:

(IV)

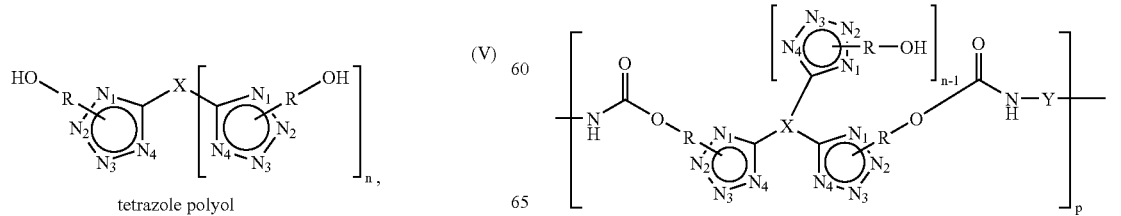

| R | X | Y |
|---|---|---|
| propyl | —(CH₂)— | hexyl |
| propyl | —(CH₂)— | 2,4-dimethyl-(methylphenyl) |
| propyl | —(CH₂)— | —(CH₂CH₂O)ₘ— |
| phenylene | —(CH₂)— | hexyl |
| phenylene | —(CH₂)— | 2,4-dimethyl-(methylphenyl) |
| phenylene | —(CH₂)— | —(CH₂CH₂O)ₘ— |
| —(CH₂CH₂O)ₘ— | —(CH₂)— | hexyl |
| —(CH₂CH₂O)ₘ— | —(CH₂)— | 2,4-dimethyl-(methylphenyl) |
| —(CH₂CH₂O)ₘ— | —(CH₂)— | —(CH₂CH₂O)ₘ— |
| propyl | —(CH₂CH₂O)ₘ— | hexyl |
| propyl | —(CH₂CH₂O)ₘ— | 2,4-dimethyl-(methylphenyl) |
| propyl | —(CH₂CH₂O)ₘ— | —(CH₂CH₂O)ₘ— |
| phenylene | —(CH₂CH₂O)ₘ— | hexyl |
| phenylene | —(CH₂CH₂O)ₘ— | 2,4-dimethyl-(methylphenyl) |
| phenylene | —(CH₂CH₂O)ₘ— | —(CH₂CH₂O)ₘ— |
| —(CH₂CH₂O)ₘ— | —(CH₂CH₂O)ₘ— | hexyl |

-continued

| R | X | Y |
|---|---|---|
| −(CH₂CH₂O)ₘ− | −(CH₂CH₂O)ₘ− | 2,4-dimethylphenyl |
| −(CH₂CH₂O)ₘ− | −(CH₂CH₂O)ₘ− | −(CH₂CH₂O)ₘ− |
| propyl | 1,4-phenylene | heptyl |
| propyl | 1,4-phenylene | 2,4-dimethylphenyl |
| propyl | 1,4-phenylene | −(CH₂CH₂O)ₘ− |
| 1,4-phenylene | 1,4-phenylene | heptyl |
| 1,4-phenylene | 1,4-phenylene | 2,4-dimethylphenyl |
| 1,4-phenylene | 1,4-phenylene | −(CH₂CH₂O)ₘ− |
| −(CH₂CH₂O)ₘ− | 1,4-phenylene | heptyl |
| −(CH₂CH₂O)ₘ− | 1,4-phenylene | 2,4-dimethylphenyl |
| −(CH₂CH₂O)ₘ− | 1,4-phenylene | −(CH₂CH₂O)ₘ− |

11. The process according to claim 7, wherein said "p" of said linear polyisocyanate polymer is about 5 to about 1,000.

12. The process according to claim 7, further comprising combining together with said tetrazole polyol (V) and said isocyanate resin (III), a catalyst selected from the group of catalysts consisting of zinc salts and dimethylaminopyridine.

13. A process for preparation of a polymer of structure (VI) comprising:

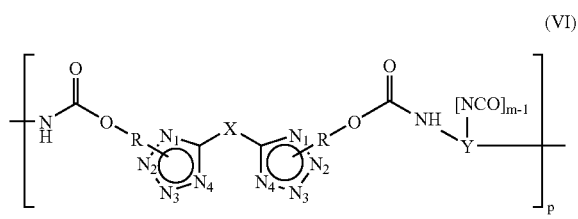
(VI)

wherein "X" is a group consisting of at least one of alkyl, aryl, and oligoether, wherein "R" is a group consisting of at least one of alkyl, aryl, and oligoether, wherein "Y" is a group consisting of at least one of alkyl, aryl, and oligoether, wherein "m" is 2 to 9, wherein "p" is about 5 to about 10,000, wherein "R" is chemically bonded to $N_1$ or $N_2$ position;

reacting an isocyanate resin with an effective amount of a tetrazole diol of structure (II),

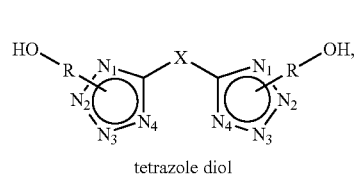
(II)
tetrazole diol at a temperature in the range from about 50° C. to about 100° C. for a time period in the range from about 1 hour to about 48 hours, wherein "X" is a group consisting of at least one of alkyl, aryl, and oligoether, wherein "R" is a group consisting of at least one of alkyl, aryl, and oligoether, wherein "R" is chemically bonded to $N_1$ or $N_2$ position;

said isocyanate resin of structure (VII),

(VII)

wherein "Y" is a group consisting of at least one of alkyl, aryl, and oligoether, wherein "m" is 2-9;

cooling to room temperature;

extracting a linear polyisocyanate polymer having the structure (VI).

14. The process according to claim 13, wherein said polymer having the structure (IV), "R", "X", and "Y" include any combination thereof:

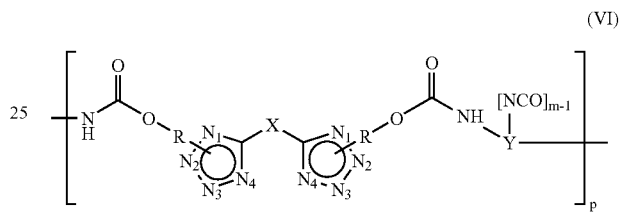
(VI)

| R | X | Y |
|---|---|---|
| ∧∨ | —(CH₂)— | ∧∨∧∨ |
| ∧∨ | —(CH₂)— | H₃C—⌬ |
| ∧∨ | —(CH₂)— | ⧼∨O⧽ₘ |
| —⌬— | —(CH₂)— | ∧∨∧∨ |
| —⌬— | —(CH₂)— | H₃C—⌬ |
| —⌬— | —(CH₂)— | ⧼∨O⧽ₘ |
| ⧼∨O⧽ₘ | —(CH₂)— | ∧∨∧∨ |

-continued

| R | X | Y |
|---|---|---|
| $-(CH_2CH_2O)_m-$ | $-(CH_2)-$ | 2,4-dimethylphenyl |
| $-(CH_2CH_2O)_m-$ | $-(CH_2)-$ | $-(CH_2CH_2O)_m-$ |
| propyl | $-(CH_2CH_2O)_m-$ | heptyl |
| propyl | $-(CH_2CH_2O)_m-$ | 2,4-dimethylphenyl |
| propyl | $-(CH_2CH_2O)_m-$ | $-(CH_2CH_2O)_m-$ |
| 1,4-phenylene | $-(CH_2CH_2O)_m-$ | heptyl |
| 1,4-phenylene | $-(CH_2CH_2O)_m-$ | 2,4-dimethylphenyl |
| 1,4-phenylene | $-(CH_2CH_2O)_m-$ | $-(CH_2CH_2O)_m-$ |
| $-(CH_2CH_2O)_m-$ | $-(CH_2CH_2O)_m-$ | heptyl |
| $-(CH_2CH_2O)_m-$ | $-(CH_2CH_2O)_m-$ | 2,4-dimethylphenyl |
| $-(CH_2CH_2O)_m-$ | $-(CH_2CH_2O)_m-$ | $-(CH_2CH_2O)_m-$ |
| propyl | 1,4-phenylene | heptyl |
| propyl | 1,4-phenylene | 2,4-dimethylphenyl |
| propyl | 1,4-phenylene | $-(CH_2CH_2O)_m-$ |
| 1,4-phenylene | 1,4-phenylene | heptyl |

-continued

| R | X | Y |
|---|---|---|
|  |  | 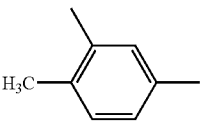 |
|  |  | 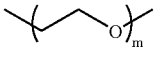 |
| 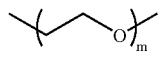 |  | 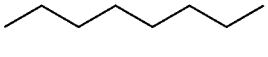 |
| 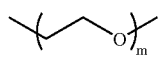 |  | 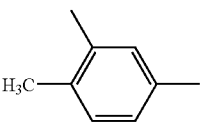 |
| 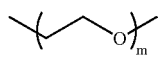 |  | 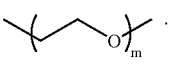 |

15. The process according to claim 13, wherein said "p" of said linear polyisocyanate polymer is about 5 to about 1,000.

16. The process according to claim 13, further comprising combining together with said tetrazole diol (II) and said isocyanate resin (VII), a catalyst selected from the group of catalysts consisting of zinc salts and dimethylaminopyridine.

17. The process according to claim 13, wherein said tetrazole diol is alkylated tetrazole diol, said alkylated tetrazole diol is di-alkylated tetrazole.

18. The process according to claim 13, wherein said tetrazole diol is arylated tetrazole diol, said arylated tetrazole diol is di-arylated tetrazole.

* * * * *